United States Patent
Hahn et al.

(10) Patent No.: US 7,364,746 B2
(45) Date of Patent: Apr. 29, 2008

(54) LIQUID CONCENTRATE FOR THE PRESERVATION OF COSMETIC AND PHARMACEUTICAL PRODUCTS

(75) Inventors: Gisela Hahn, Alveslohe (DE); Klaus Weber, Hamburg (DE); Ralf Gradtke, Tornesch (DE); Wolfgang Beilfuss, Hamburg (DE)

(73) Assignee: Air Liquide Sante (International), Paris, Cedex (FR)

( * ) Notice: Subject to any disclaimer, the term of this patent is extended or adjusted under 35 U.S.C. 154(b) by 679 days.

(21) Appl. No.: 10/649,167

(22) Filed: Aug. 26, 2003

(65) Prior Publication Data
US 2005/0100567 A1  May 12, 2005

(30) Foreign Application Priority Data
Aug. 27, 2002  (DE) .............. 102 39 238

(51) Int. Cl.
*A01N 25/34* (2006.01)
(52) U.S. Cl. .................................. 424/404
(58) Field of Classification Search .......... 424/404
See application file for complete search history.

(56) References Cited

U.S. PATENT DOCUMENTS 6,172,117 B1 *  1/2001  Bell et al. ............ 514/642
6,375,727 B1 *  4/2002  Walker ................ 106/18.32
2003/0032768 A1 *  2/2003  Stockel ............... 528/422

FOREIGN PATENT DOCUMENTS

| DE | 199 22 538 A | 11/2000 |
|----|--------------|---------|
| EP | 1 172 086 A | 1/2002 |
| EP | 1 172 102 A | 1/2002 |
| EP | 1 172 103 A | 1/2002 |
| EP | 1 206 933 A | 5/2002 |
| WO | WO 02 069716 A | 9/2002 |

OTHER PUBLICATIONS

European Search Report to EP 03 07 7431.
Rainer Gruening: "IPBC preservative combination systems for material protection"; Cosmetics and Toiletries, vol. 112, Apr. 1997, pp. 59-65, XP008024496.

* cited by examiner

*Primary Examiner*—Shelley A. Dodson
(74) *Attorney, Agent, or Firm*—Young & Thompson

(57) ABSTRACT

The invention relates to a liquid concentrate for the preservation of cosmetic and pharmaceutical products which comprises 3-iodo-2-propynyl butylcarbamate (IPBC), at least one liquid carrier selected from the group consisting of: polyvalent alcohols, glycol esters and glycol ethers, and at least one stabilizer selected from the group consisting of: formic acid, formic acid salts, and formate esters, and comprising no additional carboxylic acid selected from the group consisting of: benzoic acid, propionic acid, salicylic acid, sorbic acid, 4-hydroxybenzoic acid, dehydroacetic acid and 10-undecylenic acid and a salt thereof being present.

60 Claims, No Drawings

LIQUID CONCENTRATE FOR THE PRESERVATION OF COSMETIC AND PHARMACEUTICAL PRODUCTS

The invention relates to a liquid concentrate based on 3-iodo-2-propynyl butylcarbamate (IPBC) and to its use in the preparation and preservation of cosmetic and pharmaceutical products.

Preservatives are used in many products or systems with an aqueous phase in order to avoid harmful and spoiling effects, in particular microbial effects, on the product. Important fields of use of preservatives are cosmetic products, such as shampoos, shower gels and bath gels, but also high-value care cosmetics, such as creams, emulsions, lotions and gels. Preservatives are also used in cleaning, care and hygiene products for the home (e.g. antimicrobial hand cleansers) and body care (e.g. toothpaste).

IPBC has of late played an ever greater role in the preservation of such products. It is available as a white powder and has the disadvantage that it is only very sparingly soluble in water (approximately 0.1 g/l at 20° C.). In the solid form, it has performance disadvantages with regard to handling and metering. For this reason, industry prefers to fall back on liquid products and is interested in a liquid IPBC form.

In addition, the colour of the products is assuming an ever greater role. Colourless or pastel-coloured products, which furthermore should have a high colour stability, are increasingly desired.

For example, EP 0 757 518 is known, in accordance with which combinations of IPBC with formaldehyde-depositing compounds are used. A further example of known IPBC formulations is EP 0 484 172, in which combinations of IPBC with 1,3,5-tris(hydroxyethyl)hexahydrotriazine are described. DE 100 34 138, which describes combinations of IPBC with phenoxyethanol, is also known.

IPBC is actually sufficiently soluble in most organic solvents and compatible with many active agents, additives and auxiliaries used in cosmetics, yet the colour stability of liquid concentrates still causes great problems, which can be put down to their low solubility in water and their active groups in the IPBC molecule. Sensitivity to light, heat and oxidation are to be added, resulting in the formation of coloured decomposition products. Odour development is also frequently inadequate.

It is therefore an object of the present invention to make available a liquid product in the form of a liquid concentrate for the preservation of cosmetic and pharmaceutical products based on IPBC which is colour-stable, which, in addition to the pronounced fungicidal action, also shows a very good bactericidal action, which also is stable with reference to the active agent content and which has good organoleptic properties.

A liquid concentrate for the preservation of cosmetic and pharmaceutical products based on 3-iodo-2-propynyl butylcarbamate (IPBC) is proposed to achieve this object, which liquid concentrate is characterized in that it, in addition to IPBC, comprises a liquid carrier chosen from polyvalent alcohols, glycol esters and glycol ethers or any mixture thereof and a stabilizer chosen from formic acid, formate salts and formate esters or any mixture thereof, no additional carboxylic acid chosen from benzoic acid, propionic acid, salicylic acid, sorbic acid, 4-hydroxybenzoic acid, dehydroacetic acid and 10-undecylenic acid or a salt thereof being present.

The proportions of the individual components in the liquid concentrate given below in weight % refer to the weight of the combined concentrate, unless otherwise specified.

It has surprisingly been shown that, through the combination of IPBC with a liquid carrier and one of the formic acid derivatives mentioned as stabilizer, a product is obtained which has a stable colour, a stable active agent and an acceptable odour, without the microbiological activity being reduced.

In this connection, "colour-stabilizing action" means that the concentrate, optionally diluted with solvent or in the product to be preserved, is subject to no obvious colour change (e.g. turning brown) under conventional storage conditions. Such a colour change can, for example, be monitored with known test methods (e.g. determination of the Hazen colour number or Gardner colour number).

The term "active agent stability" means that, under conventional storage conditions over a period of at least 4 weeks, preferably 3 months, no precipitate perceptible by the senses or no cloudiness appears in the concentrate. "Conventional storage conditions" is to be understood, for example, as storage at ambient temperatures from 15 to 25° C. in dry, ventilated spaces. However, the liquid concentrate according to the invention also exhibits an improved storage stability over the period mentioned at temperatures which are clearly higher than conventional storage temperatures, preferably higher than 40° C. (e.g. 50° C.), which is particularly advantageous for use thereof in tropical regions.

The invention also relates to a process for the preparation of such a liquid concentrate and to the use of the liquid concentrate according to the invention in the preparation and/or preservation of cosmetic and pharmaceutical products.

The liquid concentrate according to the invention comprises IPBC, with reference to the total weight, in an amount of 0.01 up to 20 weight % of IPBC, preferably 0.1 up to 5 weight % of IPBC, especially 0.1 up to 2 weight % of IPBC and particularly preferably up to 1 weight % of IPBC.

The liquid concentrate comprises, as liquid carrier, a polyvalent alcohol, in particular a diol, preferably a glycol and more preferably ethylene glycol, 1,2-propylene glycol, 1,3-propylene glycol, 1,2-butylene glycol, 1,3-butylene glycol, 1,4-butylene glycol, 1,2-pentanediol, 1,3-pentanediol, 1,4-pentane-diol or 1,5-pentanediol, or a glycol ester or glycol ether, in particular an ethylene glycol, propylene glycol or butylene glycol, preferably diethylene glycol, triethylene glycol or a polyethylene glycol, or any mixture thereof. Triethylene glycol or 1,2-propylene glycol are particularly preferred.

The amount of liquid carrier present in the liquid concentrate according to the invention ranges, with reference to the total weight, from 30 to 99.989 weight %; it preferably amounts to at least 50 weight % and especially at least 95 weight %.

The stabilizer component of the liquid concentrate is chosen from formic acid, sodium formate, potassium formate, formic acid propylene glycol mono- or diester or formate esters formed in situ or any mixture thereof, in particular formic acid. 85% or 98-100% formic acid can, for example, be used.

The stabilizer component is present therein in an amount of 0.001 to 20 weight %, preferably 0.05 to 10 weight %, more preferably still 0.05 to 5 or to 2 weight % and for example less than 2 or less than 0.5 weight % or even less than 0.2 weight %.

The liquid concentrate can comprise additional active agents, functional additives and/or auxiliaries.

Polybiguanide (frequently also described as polyhexamethylenebiguanide hydrochloride) and/or a polybiguanide salt is possible as additional active agent, preferably in an amount, with reference to the total weight, of 0.1 up to 20 weight %, more preferably up to 5 weight %, particularly preferably up to 2 weight % and most preferably up to 1 weight %. For example, a 20% polyhexamethylenebiguanide hydrochloride in anhydrous or virtually anhydrous grade can be used.

The weight ratio of IPBC to polybiguanide or polybiguanide salt is in a preferred embodiment 100:1 to 1:100, preferably 10:1 to 1:10 and more preferably 1:2 to 2:1.

In an additionally preferred embodiment, the concentrate comprises $\leq 1$ weight % of IPBC, in particular 1 weight %, and $\leq 1$ weight % of polybiguanide/polybiguanide salt, in particular 0.95 weight %.

Depending on the field of application, it may be advantageous if the liquid concentrate is either anhydrous or comprises water as auxiliary, the content of water then preferably amounting to, based on the total weight, 0.01 up to 10 weight %, more preferably up to 5 weight %, more preferably still up to 4.5 or up to 4 weight %, particularly preferably up to 0.2 weight % (virtually anhydrous). The liquid concentrates are preferably anhydrous or virtually anhydrous.

The liquid concentrate can comprise, as additional active agent, in addition to or in place of the polybiguanide compound, a paraben, in particular methyl-, ethyl-, propyl- or butylparaben, a quaternary ammonium compound, in particular polyhexamethylene-biguanide or a salt thereof, a benzalkonium salt, in particular benzalkonium chloride, formaldehyde or a formaldehyde-depositing compound or a salt thereof, in particular dimethyloldimethylhydantoin (DMDMH), imidazolidinylurea, diazolidinylurea, hexetidine, 5-bromo-5-nitro-1,3-dioxane (bronidox), 2-bromo-2-nitro-1,3-propanediol (bronopol), 1,3,5,7-tetraaza-adamantane(hexamethylenetetramine), 4,4-dimethyl-1,3-oxazolidine, benzyl alcohol hemiformal, 5-ethyl-1-aza-3,7-dioxabicyclo[3.3.0]octane, 1-(3-chloroallyl)-3,5,7-triaza-1-azoniaadamantane chloride or mixtures thereof, phenoxyethanol, phenoxypropanol, benzyl alcohol, a halogen compound, in particular dibromodicyanobutane (DBDCB), an amidine compound, in particular hexamidine or dibromohexamidine, or a salt thereof, or an isothiazolone, in particular N-methylisothiazolone or N-octylisothiazolone, or any mixture of the abovementioned compounds.

Preferred antimicrobial active agents which can be used to improve the effectiveness and/or to broaden the spectrum of activity are o-phenylphenol and its salts, zinc pyrithione, inorganic sulphites and bisulphites, sodium iodate, dibromohexamidine and its salts, triclocarban, 4-chloro-m-cresol, triclosan, 4-chloro-3,5-dimethylphenol, 2-hydroxy-4,4'-dichlorophenyl ether (e.g. Tinosan HP 100), polyhexamethylenediguanide and its salts, 1-(4-chlorophenoxy)-1-(imidazol-1-yl)-3,3-dimethyl-2-butanone, 1-hydroxy-4-methyl-6-(2,4,4-trimethylpentyl)-2-pyridone and its monoethanolamine salt, 1,2-dibromo-2,4-dicyanobutane, bromochlorophen, 5-chloro-2-methyl-3(2H)-isothiazolone, 2-methyl-3(2H)-isothiazolone, 2-benzyl-4-chlorophenol, 2-chloroacetamide, chlorohexidine and its salts, N-[($C_{12}$-$C_{22}$) alkyltrimethyl]ammonium salts, hexamidine and its salts, glutaraldehyde, silver chloride, benzethonium chloride, benzalkonium salts (e.g. benzalkonium chloride), or mixtures of the abovementioned compounds.

In addition, a large number of substances or combinations of substances can be used as additional functional additives, auxiliaries or active agents (cosmetic additives) for the basic formulation (in place of the acids mentioned below, the corresponding salts are optionally used). The additives can be anion-active or cation-active. Examples of additives are skin care substances and moisture-retaining factors (e.g. urea or Sensiva SC 50), complexing agents (e.g. EDTA), essential oils and natural extracts, amphoteric surfactants, surfactants, cleaning additives and disinfection active agents (e.g. cocoamidopropyl betaine), fragrances, antiacne or antidandruff active agents (e.g. octopirox and Lipacid C8G), fungicides, dyes, corrosion inhibitors, disinfection active agents and antiseptics (e.g. octenidine dihydrochloride), bitter principals (e.g. denatonium salts), screening agents (e.g. 2-phenylbenzimidazolesulphonic acid), deodorant active agents (e.g. zinc phenolsulphonate or Sensiva SC 50), oral care active agents (e.g. potassium monofluorophosphate), isothiazolones, carbohydrate compounds (e.g. alkylpolyglycosides, starch or cellulose derivatives and cyclodextrins), alkali metal chlorides (e.g. NaCl or KCl), anionic surfactants (e.g. lauryl ether sulphates), plant extracts and oils. Quaternary ammonium salts (e.g. cetyltrimethylammonium chloride or bromide, cetylpyridinium chloride or didecyldimethylammonium chloride) can be used as possible cation-active active agents.

Many of these cosmetic additives also have a multifunctional action. In some cases, synergistic increases in activity of the liquid concentrates according to the invention with the additives may also arise.

Additional additives, auxiliaries and/or active agents are, for example, thickeners, buffers, antifoaming agents, solubility promoters, antistatic agents, polymers and/or antioxidants.

In individual cases, the type and amount of additional active agents can be established by a person skilled in the art in a simple and rapid manner by a few experiments, it being possible for the active agent system obtained, which includes the liquid concentrate according to the invention, to have a broad or also very specific application potential.

The preparation of the concentrates is carried out by simple mixing. For example, the solid components are dissolved with stirring in the liquid components and the additional additives and auxiliaries are stirred in homogeneously. The mixture is optionally heated (e.g. up to 50° C.).

With regard to the preparation process, in which the constituents are mixed with one another in any sequence, it is optionally advantageous for the liquid concentrate to be stirred or allowed to stand at an increased temperature for a period of time. This temperature treatment results in a surprisingly increased stability. In the course of this, the mixture is advantageously, subsequent to the mixing together, held for 0.5 to 48 hours at a temperature of 30 to 70° C., optionally with stirring, in particular 30 up to 60° C., more preferably at 30 up to 50° C. For example, a temperature treatment over 6 h at 50° C., 24 h at 40° C. or 48 h at 30° C. is possible. The higher the temperature, the shorter the period of time of the temperature treatment can be.

It is advantageous that the liquid concentrates according to the invention can be incorporated in the cosmetic and pharmaceutical products by simple dilution. This offers handling and cost advantages compared with the use of individual substances, which are often powders or granules and have to be dissolved or dispersed before incorporation in the product to be preserved. Storage and transportation costs can also be reduced by the concentrate form.

A further advantage is that the liquid concentrates according to the invention are suitable as solubility promoters for cosmetic additives with little or limited solubility in water or as solvents or carriers for various cosmetic additives.

The liquid concentrate according to the invention preferably exists as a clear homogeneous solution. However, should precipitates possibly arise at a low pH in the concentrate or in predilutions, these can be reversibly dissolved by simple dilution or by correcting the pH. However, it is also possible to prepare the liquid concentrate as a homogeneous-disperse preparation, it being preferable in such cases to avoid relatively large amounts of crystallized active agents in the preparation. In addition, the liquid concentrate can exist in the form of a paste.

In a preferred embodiment, an "aged" mixture of glycols and/or glycol ethers and formic acid is used as carrier/stabilizer combination. The expression "aged" means in this connection that combinations of glycols and/or glycol ethers and formic acid are held at an increased temperature (up to boiling point of the mixture) for a sufficiently long period of time, optionally with stirring, until the smell of formic acid has largely or completely disappeared. Ester formation between the formic acid and the glycol and/or glycol ether possibly occurs during this ageing, the exact structure of the compounds formed being unknown. Alternatively, glycol (ether) formates can also be dissolved in glycol and/or glycol ether and the combination can be used together with the IPBC.

Liquid concentrates which smell very little or not at all of formic acid are particularly preferred.

The pH of the liquid concentrate is 1 to 10, preferably 3 to 7 and preferably 5 to 7 (measured after preparation of a fresh solution or emulsion with water). For example, the pH of a 2 weight % solution/emulsion in water ranges from 2.5 to 5.5 or approximately 3.

The liquid concentrates according to the invention therefore have, in particular, the following advantages:
 liquid;
 concentrate form;
 handling and cost advantages;
 homogeneous;
 limpid;
 low viscosity;
 colourless to faintly coloured;
 odourless or virtually odourless;
 very good thermal stability;
 very good colour stability;
 very good active agent stability;
 broad spectrum of activity with improved (synergistic) effectiveness compared with known IPBC products;
 can, during the production of cosmetics, serve as solvent, solubility promoter or carrier for other ingredients (e.g. fragrance, or the like);
 safe—no residue risk upon use;
 stable at low temperatures, liquid and pumpable at low temperatures (even after 12 months at, e.g., −5° C.); and
 miscible, compatible with a wide range of ingredients.

The liquid concentrates according to the invention are suitable for the preparation of cosmetic products, in particular for leave-on products, such as creams, lotions, gels or moist wipes, the pH values of which generally range from 5 to 8, or for rinse-off products, such as shampoos, the pH values of which are generally less than 7, in particular less than 6.

Furthermore, the liquid concentrates according to the invention are suitable as additive for pharmaceutical products and for washing, cleaning, care, body care and hygiene products. In addition to the preservation, the concentrates according to the invention contribute to the antimicrobial effectiveness.

The invention is illustrated below by means of examples.

EXAMPLES

In the examples and comparative examples, polybiguanide was used as a 20 weight % product in water; i.e. 4.75 weight % of 20% polybiguanide corresponds to 0.95 weight % of active agent.

The following formulations were prepared by introducing the liquid carrier, adding the IPBC and the polybiguanide and then stirring until a clear solution was formed. The stabilizer was then added and homogeneously distributed with stirring. Clear solutions were obtained by doing this.

Example 1

| | |
|---|---|
| 1.00 weight % | IPBC |
| 4.75 weight % | 20% Polybiguanide |
| 2.50 weight % | 98-100% Formic acid |
| 91.75 weight % | Triethylene glycol |

Example 2

| | |
|---|---|
| 1.00 weight % | IPBC |
| 4.75 weight % | 20% Polybiguanide |
| 0.50 weight % | 97% Sodium formate |
| 93.75 weight % | 1,3-Butanediol |

Example 3

| | |
|---|---|
| 1.00 weight % | IPBC |
| 4.75 weight % | 20% Polybiguanide |
| 2.90 weight % | Formic acid (85% in water) |
| 91.35 weight % | 1,2-Propylene glycol |

Example 4

| | |
|---|---|
| 0.95 weight % | IPBC |
| 4.75 weight % | 20% Polybiguanide |
| 2.20 weight % | Formic acid (85% in water) |
| 92.10 weight % | 1,2-Propylene glycol |

COMPARATIVE EXAMPLES

Comparative Example 1

| | |
|---|---|
| 1.00 weight % | IPBC |
| 4.75 weight % | 20% Polybiguanide |
| 94.25 weight % | 1,2-Propylene glycol |

Comparative Example 2

| | |
|---|---|
| 1.00 weight % | IPBC |
| 4.75 weight % | 20% Polybiguanide |
| 94.25 weight % | Triethylene glycol |

Comparative Example 3

| | |
|---|---|
| 1.00 weight % | IPBC |
| 4.75 weight % | 20% Polybiguanide |
| 1.0 weight % | Glycolic acid |
| 93.25 weight % | Triethylene glycol |

Comparative Example 4

| | |
|---|---|
| 1.00 weight % | IPBC |
| 4.75 weight % | 20% Polybiguanide |
| 1.0 weight % | Lactic acid (80-90%) |
| 93.25 weight % | Triethylene glycol |

Comparative Example 5

| | |
|---|---|
| 1.00 weight % | IPBC |
| 4.75 weight % | 20% Polybiguanide |
| 1.0 weight % | Benzoic acid (>99.5%) |
| 93.25 weight % | Triethylene glycol |

Comparative Example 6

| | |
|---|---|
| 1.00 weight % | IPBC |
| 4.75 weight % | 20% Polybiguanide |
| 1.0 weight % | Formic acid (98-100%) |
| 93.25 weight % | Phenoxyethanol |

The examples according to the invention all showed good stability with regard to odour, colour and active agent, while the products of the comparative examples did not display sufficient stability with regard to odour, colour and active agent.

The results of these investigations are collated in Tables 1 and 2.

TABLE 1

Storage stability, low-temperature stability and colour stability of the liquid concentrates

| | | Example 1 | Example 3 | Example 4 | Comparative Example 1 |
|---|---|---|---|---|---|
| Appearance immediately after preparation | | clear liquid/ colourless | clear liquid/ colourless | clear liquid/ colourless | clear liquid/almost colourless |
| Zero values | Odour | pungent | pungent | pungent | almost neutral |
| | Colour number/Hazen | 14 | 6 | 6 | 27 |
| | IPBC (%) | 1.00 | 0.96 | 0.92 | 0.98 |
| | Polybiguanide (%) | 0.97 | 0.94 | 0.98 | 0.98 |
| 3 Months storage in blue polyethylene bottles | | | | | |
| Appearance | | All samples through all following storage conditions o.V. (clear liquids) | | | |
| −5° C. | Odour | not pungent | not pungent | not pungent | almost neutral |
| | Colour number/Hazen | 99 | 6 | 7 | 74 |
| | IPBC (%) | 0.98 | 1.00 | 0.94 | 0.98 |
| | Polybiguanide | 1.00 | 0.94 | 0.93 | 1.01 |
| 4° C. | Odour | not pungent | not pungent | not pungent | almost neutral |
| | Colour number/Hazen | 64 | 97 | 8 | 553 |
| | IPBC (%) | 0.98 | 0.99 | 0.93 | 0.98 |
| | Polybiguanide | 1.01 | 0.95 | 0.94 | 1.01 |
| 25° C. | Odour | not pungent | not pungent | not pungent | almost neutral |
| | Colour number/Hazen | 33 | 16 | 16 | 346 |
| | IPBC (%) | 0.97 | 0.97 | 0.89 | 0.88 |
| | Polybiguanide | 1.02 | 0.96 | 0.96 | 1.02 |
| ATL (ambient temperature/light) | Odour | not pungent | not pungent | not pungent | almost neutral |
| | Colour number/Hazen | 30 | 9 | 10 | 422 |
| | IPBC (%) | 0.97 | 0.97 | 0.95 | 0.87 |
| | Polybiguanide | 1.01 | 0.96 | 0.95 | 1.01 |
| Window/South | Odour | not pungent | not pungent | not pungent | almost neutral |
| | Colour number/Hazen | 78 | 22 | 21 | 773 |
| | IPBC (%) | 0.94 | 0.96 | 0.95 | 0.77 |
| | Polybiguanide | 1.02 | 0.97 | 0.97 | 1.02 |
| 40° C. | Odour | not pungent | not pungent | not pungent | almostneutral |
| | Colour number/Hazen | 189 | 568 | 495 | 560 |
| | IPBC (%) | 0.88 | 0.65 | 0.66 | 0.58 |
| | Polybiguanide | 1.04 | 1.01 | 1.00 | 1.03 |

TABLE 2

Storage stability, low-temperature stability and colour stability of liquid concentrates according to the invention

|  | Comparative Example 3 | Comparative Example 4 | Comparative Example 5 | Comparative Example 6 | Example 2 |
|---|---|---|---|---|---|
| Appearance immediately after preparation | clear, colourless | clear, colourless | clear, colourless | clear, colourless | clear, colourless |
| Hazen colour number | 7 | 9 | 9 | 5 | 5 |
| Odour | characteristic | characteristic | characteristic | pungent | not pungent |
| IPBC content | 0.98 | 1.01 | 1.03 | 1.01 | 1.00 |
| After storage for 4 weeks at ambient temperature/light in a glass jar: | | | | | |
| Appearance | clear | clear | clear | clear | clear |
| Hazen colour number | >1 000 | >1 000 | >1 000 | >1 000 | 5 |
| Gardner colour number | 6.4 | 6.4 | 5.8 | 0 | 0 |
| Odour | o.V. | o.V. | o.V. | not pungent | o.V. |
| After storage for 4 weeks at +50° C. in a glass jar: | | | | | |
| Appearance | clear | clear | clear | clear | clear |
| Hazen colour number | >1 000 | >1 000 | >1 000 | >1 000 | 122 |
| Gardner colour number | 5.4 | 5.4 | 5.5 | 6.6 | 0.4 |
| Odour | o.V. | o.V. | o.V. | not pungent | o.V. |
| IPBC content | 0.76% | 0.74% | 0.72% | 0.45% | 0.96% |
| IPBC loss in % | 22% | 27% | 30% | 55% | 4% |

It follows from Tables 1 and 2 that the liquid concentrate according to the invention show a clearly improved stability.

For the colour stability investigations, the liquid concentrates were stored in clear glass and the Hazen or Gardner colour number (see test methods) was determined immediately after preparation on a freshly produced preparation, and also after the period of time given and storage at the temperatures given.

Test Methods:

The Hazen colour number (DIN-ISO 6271, also known as "APHA method" or "platinum/cobalt scale") is defined as mg of platinum per 1 litre of solution. For the Hazen stock solution, 1.246 g of potassium hexachloro-platinate(IV) and 1.00 g of cobalt(II) chloride are dissolved in 100 ml of hydrochloric acid and made up to 1000 ml with distilled water. The Hazen colour scale is used for assessing the colour of products which are almost limpid. It is graduated more closely in the light-yellowish region than the iodine colour scale and extends as far as limpid shades of colour.

The Gardner colour number is defined in DIN-ISO 4630. The light-yellow Gardner colour numbers (1 to 8) are based on potassium chloroplatinate solutions and the colour numbers 9 to 18 on iron(III) chloride, cobalt(II) chloride and hydrochloric acid solutions.

The respective concentrate was introduced into a cell and then the colour number was measured using a calorimeter of Lico® 200 type (Dr Lange GmbH, Berlin).

The odour development was examined organoleptically. The odours were in each case assessed by 3 people.

The invention claimed is:

1. A liquid concentrate preservative, comprising:
   a) 3-iodo-2-propynyl butylcarbamate (IPBC);
   b) at least one liquid carrier;
   c) at least one stabilizer; and
   d) polyhexamethylene biguanide, or a salt thereof, wherein,
   the weight ratio of said IPBC to said polyhexamethylene biguanide is from about 100:1 to about 1:100, and
   no additional carboxylic acid chosen from benzoic acid, propionic acid, salicylic acid, sorbic acid, 4-hydroxybenzoic acid, dehydroacetic acid, and 10-undecylenic acid, or the salts thereof, is present.

2. The concentrate according to claim 1, wherein said IPBC is from about 0.01% to about 20% by weight of the concentrate.

3. The concentrate according to claim 2, wherein said IPBC is up to about 5% by weight.

4. The concentrate according to claim 3, wherein said IPBC is up to about 2% by weight.

5. The concentrate according to claim 4, wherein said IPBC is up to about 1% by weight.

6. The concentrate according to claim 1, wherein said liquid carrier comprises at least one component selected from the group consisting of:
   a) polyvalent alcohols;
   b) glycol esters; and
   c) glycol ethers.

7. The concentrate according to claim 6, wherein said polyvalent alcohol is at least one component selected from the group consisting of:
   a) diol;
   b) glycol;
   c) ethylene glycol;
   d) 1,2-propylene glycol;
   e) 1,3-propylene glycol;
   f) 1,2-butylene glycol;
   g) 1,3-butylene glycol;
   h) 1,4-butylene glycol;
   i) 1,2-pentanediol;
   j) 1,3-pentanediol;
   k) 1,4-pentanediol;
   l) 1,5-pentanediol;
   m) glycol ester;
   n) glycol ether;
   o) ethylene glycol;
   p) propylene glycol;
   q) butylene glycol;
   r) diethylene glycol;
   s) triethylene glycol;
   t) polyethylene glycol;
   u) triethylene glycol; and
   v) 1,2-propylene glycol.

8. The concentrate according to claim 1, wherein said stabilizer comprises at least one component selected from the group consisting of:
   a) formic acid;
   b) formate salts;
   c) formate esters;
   c) sodium formate;
   e) potassium formate; and
   f) formic acid propylene glycol mono-, diester, and formate esters formed in situ.

9. The concentrate according to claim 8, wherein said stabilizer consists of formic acid.

10. The concentrate according to claim 1, wherein said stabilizer is from about 0.001% to about 20% by weight of the concentrate.

11. The concentrate according to claim 10, wherein said stabilizer is up to about 10% by weight.

12. The concentrate according to claim 11, wherein said stabilizer is up to about 5% by weight.

13. The concentrate according to claim 12, wherein said stabilizer is up to about 2% by weight.

14. The concentrate according to claim 13, wherein said stabilizer is less than about 0.5% by weight.

15. The concentrate according to claim 14, wherein said stabilizer is less than about 0.2% by weight.

16. The concentrate according to claim 1, further comprising:
   a component selected from the group consisting of:
   a) at least one functional additive;
   b) at least one auxiliary; and
   c) mixtures thereof.

17. The concentrate according to claim 15, wherein said polyhexamethylene biguanide is up to about 20% by weight of the concentrate.

18. The concentrate according to claim 17, wherein said polyhexamethylene biguanide is up to about 5% by weight.

19. The concentrate according to claim 18, wherein said polyhexamethylene biguanide is up to about 2% by weight.

20. The concentrate according to claim 19, wherein said polyhexamethylene biguanide is up to about 1% by weight.

21. The concentrate according to claim 15, wherein said weight ratio ranges from about 10:1 to about 1:10.

22. The concentrate according to claim 15, wherein said weight ratio ranges from about 1:2 to about 2:1.

23. The concentrate according to claim 1, wherein said IPBC is less than about 1% by weight of the concentrate, and said polyhexamethylene biguanide is less than about 1% by weight of the concentrate.

24. The concentrate according to claim 23, wherein said IPBC is about 1% by weight and said polyhexamethylene biguanide is less than about 1% by weight.

25. The concentrate according to claim 24, wherein said IPBC is about 1% by weight and said polyhexamethylene biguanide is about 0.95% by weight.

26. The concentrate according to claim 25, wherein said IPBC is less than about 1% by weight and said polyhexamethylene biguanide is about 0.95% by weight.

27. The concentrate according to claim 1, further comprising:
   (d) at least one functional additive; and
   (e) absent an auxiliary.

28. The concentrate according to claim 16, wherein said auxiliary comprises water.

29. The concentrate according to claim 28, wherein said water is from about 0.01% to about 10% by weight of the concentrate.

30. The concentrate according to claim 29, wherein said water is up to about 5% by weight.

31. The concentrate according to claim 30, wherein said water is up to about 4.5% by weight.

32. The concentrate according to claim 31, wherein said water is up to about 4% by weight.

33. The concentrate according to claim 32, wherein said water is up to about 0.2% by weight.

34. The concentrate according to claim 16, further comprising a paraben.

35. The concentrate according to claim 34, wherein said paraben is selected from the group consisting of: methyl-, ethyl-, propyl- and butylparaben.

36. The concentrate according to claim 16, further comprising: a quaternary ammonium compound.

37. The concentrate according to claim 16, further comprising: a halogen compound.

38. The concentrate according to claim 37, wherein said halogen compound is dibromodicyanobutane (DBDCB).

39. The concentrate according to claim 16, further comprising: an amidine compound.

40. The concentrate according to claim 39, wherein said amidine compound is at least one component selected from the group consisting of:
   a) hexamidine;
   b) dibromohexamidine; and
   c) the salts thereof.

41. The concentrate according to claim 16, further comprising: isothiazolone.

42. The concentrate according to claim 41, wherein said isothiazolone is one of N-methylisothiazolone and N-octyhsothiazolone.

43. The concentrate according to claim 16, further comprising: at least one component selected from the group consisting of:
   a) paraben;
   b) quaternary ammonium compound;
   c) benzalkonium salt;
   d) formaldehyde or a formaldehyde-depositing compound or a salt thereof;
   e) phenoxyethanol;
   f) phenoxypropanol;
   g) benzyl alcohol;
   h) halogen compound;
   i) amidine compound; and
   j) isothiazolone.

44. The concentrate according to claim 43, wherein said paraben comprises at least one component selected from the group consisting of: methyl-, ethyl-, propyl-, and butylparaben.

45. The concentrate according to claim 43, wherein said halogen compound is dibromodicyanobutane (DBDCB)

46. The concentrate according to claim 43, wherein said amidine compound, is at least one component selected from the group consisting of:
   a) hexamidine;
   b) dibromohexamidine; and
   c) the salts thereof.

47. The concentrate according to claim 43, wherein said isothiazolone is one of N-methylisothiazolone and N-octyl-isothiazolone.

48. The concentrate according to claim 1, wherein a process for the preparation of a concentrate comprises mixing constituents of the concentrate.

49. The concentrate according to claim 48, wherein said mixture is subsequently held after mixing for about 0.5 hour to about 48 hours at a temperature from about 30° C. to about 70° C.

50. The concentrate according to claim 49, wherein said temperature ranges from about 30° C. to about 60° C.

51. The concentrate according to claim 50, wherein said temperature ranges from about 30° C. to 50° C.

52. The concentrate according to claim 1, wherein said concentrate may be utilized for the preparation of cosmetic and pharmaceutical products.

53. The concentrate according to claim 1, wherein said concentrate may be utilized for the preservation of cosmetic and pharmaceutical products.

54. The concentrate according to claim 16, further comprising a benzalkonium salt.

55. concentrate according to claim 54, wherein said salt is benzalkonium chloride.

56. The concentrate according to claim 16, further comprising: formaldehyde or a formaldehyde-depositing compound or a salt thereof.

57. The concentrate according to claim 56, wherein said formaldehyde-depositing compound is at least one component selected from the group consisting of: dimethyloldimethylhydantoin (DMDMH), imidazolidinylurea, diazolidinylurea, hexetidine, 5-bromo-5-nitro-1, 3-dioxane (bronidox), 2-bromo-2nitro-1, 3-propanediol (bronopol), 1,3,5,7-tetraazaadamantane (hexamethylenetetramine), 4, 4-dimethyl-1, 3-oxazolidine, benzyl alcohol hemiformal, 5ethyl-1-aza-3,7-dioxabicyclo[3,3.0]octane, and 1-(3-chloroallyl)-3,5,7-triaza-1-azoniaadamantane chloride.

58. The concentrate according to claim 16, further comprising: at least one of phenoxyethanol, phenoxypropanol, and benzyl alcohol.

59. The concentrate according to claim 43, wherein said benzalkonium salt is benzalkonium chloride.

60. The concentrate according to claim 43, wherein said formaldehyde-depositing compound is at least one component selected from the group consisting of: dimethyloldimethylhydantoin (DMDMH), imidazolidinylurea, diazolidinylurea, hexetidine, 5-bromo-5-nitro-1,3-dioxane (bronidox), 2bromo-2-nitro-1,3-propanediol (bronopol), 1,3,5,7-tetraazaadamantane (hexamethylenetetramine), 4,4-dimethyl-1,3-oxazolidine, benzyl alcohol hemiformal, 5-ethyl-1-aza-3,7-dioxabicyclo[3,3.0]octane, and 1-(3-chloroallyl)-3,5,7-triaza-1-azoniaadamantane chloride.

* * * * *